United States Patent

Metzger et al.

[11] 4,093,447
[45] June 6, 1978

[54] N-ARYLCARBAMIC ACID ESTERS AND PLANT GROWTH REGULANT COMPOSITIONS AND METHODS

[75] Inventors: Carl Metzger, Wuppertal-Vohwinkel; Gerhard Jäger, Wuppertal-Elberfeld; Klaus Lürssen, Koenigsdorf, all of Germany

[73] Assignee: Bayer Aktiengesellschaft, Leverkusen, Germany

[21] Appl. No.: 632,742

[22] Filed: Nov. 17, 1975

Related U.S. Application Data

[62] Division of Ser. No. 265,909, Jun. 23, 1972, Pat. No. 3,920,727.

[30] Foreign Application Priority Data

Jun. 23, 1971 Germany ............................... 2131028
Mar. 23, 1972 Germany ............................... 2214057

[51] Int. Cl.² ........................ A01N 9/20; C07C 125/06
[52] U.S. Cl. ............................................ 71/111; 71/77; 71/98; 71/108; 560/10; 560/16; 560/17; 560/27; 560/28; 560/29
[58] Field of Search ............... 260/471 C, 470; 560/27, 560/28, 29, 16, 17, 10; 71/111, 108, 98

[56] References Cited

U.S. PATENT DOCUMENTS

2,863,488  12/1958  Short et al. .................... 260/471 C
2,954,396  9/1960  Ayers et al. .................... 260/471 C

FOREIGN PATENT DOCUMENTS

664,448  11/1965  Belgium ........................ 260/471 C
1,213,395  3/1966  Germany ....................... 260/471 C

*Primary Examiner*—Jane S. Myers

*Attorney, Agent, or Firm*—Burgess, Dinklage & Sprung

[57] ABSTRACT

New N-arylcarbamic acid esters of the formula

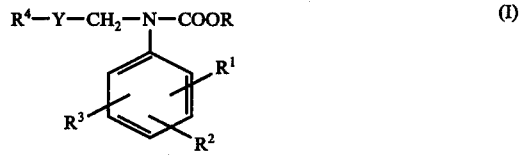

in which
R is lower aliphatic hydrocarbyl, optionally substituted,
$R^1$, $R^2$ and $R^3$, which may be identical or different, are each hydrogen, alkyl, cycloalkyl, alkoxy, haloalkyl or halogen,
$R^4$ is alkyl, alkenyl, alkynyl, cycloalkenyl, haloalkyl, haloalkenyl, haloalkynyl, alkoxyalkyl or alkylthioalkyl, acylalkyl (i.e., alkanoyloxyalkyl), alkoxycarbonylalkyl, carbalkoxyalkyl, carbalkoxyalkenyl, or an optionally substituted cycloalkyl, aryl, aralkyl, aryloxyalkyl or arylthioalkyl radical, or the grouping

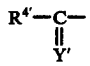

wherein
$R^{4'}$ is hydrogen or is defined as $R^4$ is defined above, and
Y and Y' are oxygen or sulfur.

are outstanding effective in regulating the growth of plants, i.e., to inhibit, stimulate or alter the growth of plants.

20 Claims, No Drawings

N-ARYLCARBAMIC ACID ESTERS AND PLANT GROWTH REGULANT COMPOSITIONS AND METHODS

This is a division of application Ser. No. 265,090, filed June 23, 1972, now U.S. Pat. No. 3,920,727.

The present invention relates to certain new N-arylcarbamic acid esters, to their use as plant-growth-regulating agents, and to plant-growth-regulating compositions containing them.

It has already been disclosed that maleic acid hydrazide can be used for keeping down plant growth and for suppressing undesired side-shoots in tobacco or in tomatoes. However, its inhibiting action is not always entirely satisfactory if low amounts and concentrations are used. Equally, its toleration by plants is not always good, especially at high concentrations (see U.S. Pat. Nos. 2,575,954, 2,614,916 and 2,805,926; British Patent Specification 672,596; and W. H. Andrew and S. R. Andrew, Can. I. Biol. 31, 426 (1953)).

The present invention provides, as new compounds, N-arylcarbamic acid ester compounds of the general formula

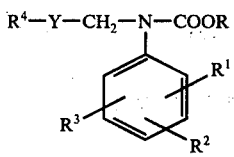

in which
R is lower aliphatic hydrocarbyl by which is meant a hydrocarbon radical containing up to about 10 carbon atoms, e.g., open-chain aliphatic, which can be saturated or olefinically or acetylenically unsaturated, or cycloaliphatic, and lower aliphatic hydrocarbyl substituted with hydroxy, halogen, alkoxy, or aryl, wherein the alkoxy or aryl are also lower, i.e., contain up to about 10 carbon atoms; more specifically R is alkyl, alkenyl, alkynyl, cycloalkyl, hydroxyalkyl, hydroxyalkenyl, hydroxyalkynyl, haloalkyl, haloalkenyl, haloalkynyl, alkoxyalkyl or aralkyl that may be substituted in the aryl part, $R^1$, $R^2$ and $R^3$, which may be identical or different, are each hydrogen, alkyl, cycloalkyl, alkoxy, haloalkyl or halogen, $R^4$ is alkyl, alkenyl, alkynyl, cycloalkenyl, haloalkyl, haloalkenyl, haloalkynyl, alkoxyalkyl or alkylthioalkyl, acylalkyl (i.e., alkanoyloxyalkyl), alkoxycarbonylalkyl, carbalkoxyalkyl, carbalkoxyalkenyl, or an optionally substituted cycloalkyl, aryl, aralkyl, aryloxyalkyl or arylthioalkyl radical, or the grouping

wherein
$R^{4'}$ is hydrogen or is defined as $R^4$ is defined above and
Y and Y' are oxygen or sulfur.

In formula (I) it is preferred that R should be straight-chain or branched alkyl with 1 to 4 carbon atoms, straight-chain or branched alkenyl with 3 to 6 carbon atoms, straight-chain or branched alkynyl with 3 to 6 carbon atoms, cycloalkyl with 5 to 8 carbon atoms, hydroxyalkyl with 2 to 4 carbon atoms, hydroxyalkenyl or hydroxyalkynyl with, in either case, 3 to 6 carbon atoms, alkoxyalkyl with 1 to 4 carbon atoms in the alkoxy part and 2 to 4 carbon atoms in the alkyl part, haloalkyl with 1 to 4 carbon atoms and 1 to 3 halogen atoms (especially fluorine and chlorine), haloalkenyl or haloalkynyl with, in either case, 3 to 6 carbon atoms and 1 to 3 halogen atoms (especially chlorine) or aralkyl with 1 to 4 carbon atoms in the alkyl part and 6 to 10 carbon atoms in the aryl part, this aryl part optionally carrying one or more substituents, preferably selected from halogen (especially fluorine, chlorine or bromine), branched or straight-chain alkyl with 1 to 4 carbon atoms, haloalkyl with 1 to 4 carbon atoms and 1 to 3 halogen atoms, alkoxy with up to 4 carbon atoms and nitro;

that $R^1$, $R^2$ and $R^3$, which may be alike or different, should each be hydrogen, fluorine, chlorine, bromine, straight-chain or branched alkyl with 1 to 4 carbon atoms, cycloalkyl with 5 to 7 carbon atoms, straight-chain or branched alkoxy with 1 to 4 carbon atoms, haloalkyl with 1 or 2 carbon atoms and 2 to 5 halogen atoms (especially fluorine or chlorine);

and that $R^4$ should be straight-chain or branched alkyl with 1 to 6 carbon atoms or haloalkyl with 1 to 6 carbon atoms and 1 to 3 halogen atoms (especially fluorine or chlorine), straight-chain or branched alkenyl with 3 to 6 carbon atoms or haloalkenyl with 3 to 6 carbon atoms and 1 to 4 halogen atoms (especially fluorine or chlorine), straight-chain or branched alkynyl with 3 to 6 carbon atoms or haloalkynyl with 3 to 6 carbon atoms and 1 to 4 halogen atoms (especially fluorine or chlorine), alkoxyalkyl, alkylthioalkyl or acylalkyl or alkoxycarbonylalkyl, carbalkoxyalkyl, carbalkoxyalkenyl with 1 to 4 carbon atoms in the alkoxy or alkylthio or acyl (i.e., alkanoyl) part and 1 to 4 carbon atoms in the alkyl part, optionally substituted cycloalkyl with 3 to 8 carbon atoms in the cycloalkyl part, aryl with 6 to 10 carbon atoms, or aralkyl, aryloxyalkyl or arylthioalkyl with, in each case, 6 to 10 carbon atoms in the aryl part and 1 to 3 carbon atoms in the alkyl part, the aryl part of the four last-mentioned radicals optionally carrying one or more substituents selected from halogen (preferably fluorine, chlorine or bromine), straight-chain or branched alkyl or alkoxy with, in either case, 1 to 3 carbon atoms and haloalkyl with 1 or 2 carbon atoms and 1 to 5 halogen atoms (especially fluorine or chlorine), or the grouping $R^{4'}$—CY'—, where Y' is oxygen or sulphur and $R^{4'}$ is hydrogen or is defined as $R^4$ has just been defined above.

The compounds of the formula (I) have been found to possess very good plant-growth-influencing properties. Surprisingly, the N-arylcarbamic acid esters according to the invention show a considerably greater inhibiting action on plant growth and far greater toleration by plants than maleic acid hydrazide, which is known from the state of the art and which is the nearest active substance of the same type of action. The compounds according to the invention hence represent a valuable enrichment of the art.

The present invention also provides a process for the preparation of an N-arylcarbamic acid ester of the formula (I) in which an N-chloromethyl-N-arylcarbamic acid ester of the general formula

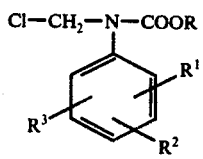 (II)

in which R, R$^1$, R$^2$ and R$^3$ have the meanings stated above,
is reacted (a) with a compound of the general formula

H—Y—R$^4$ (III)

in which R$^4$ and Y have the meanings stated above, in the presence of an acid-binding agent and optionally in the presence of a solvent or (b) with a compound of the general formula

A—Y—R$^4$ (IV)

in which
R$^4$ and Y have the meanings stated above, and
A is a cation or a fraction of a cation, such as an ammonium, alkylammonium, dialkylammonium, trialkylammonium, alkali metal or alkaline earth metal cation,
in the presence of a solvent.

If Isopropyl-N-chloromethyl-N-(3-chlorophenyl)-carbamate and n-propylmercaptan are used as starting Methyl-N-chloromethyl-N-(3,4-dichlorophenyl)-carbamate, Isopropyl-N-chloromethyl-N-(2,5-dichlorophenyl)-carbamate, 2-Chloroethyl-N-chloromethyl-N-(2,5-dichlorophenyl)-carbamate, Isopropyl-N-chloromethyl-N-(2-methyl-5-chlorophenyl)-carbamate, 2-Chloroethyl-N-chloromethyl-N-(2-methyl-5-chlorophenyl)-carbamate, Isopropyl-N-chloromethyl-N-(2-methoxy-5-chlorophenyl)-carbamate, 2-Chloroethyl-N-chloromethyl-N-(2-methoxy-5-chlorophenyl)-carbamate, Isopropyl-N-chloroethyl-N-(3-methylphenyl)-carbamate and Isopropyl-N-chloromethyl-N-(3-trifluoromethylphenyl)-carbamate.

The N-chloromethyl-N-aryl carbamates of the formula (II) used as starting materials have not hitherto been described in the literature, but can be prepared by a process, which does not form part of the state of the art, that comprises reacting carbamic acid esters with paraformaldehyde in the presence of thionyl chloride in an inert solvent at temperatures between +10° and +120° C. This process is the subject of a separate patent application.

Preferably, in formula (IV), A is ammonium, dialkylammonium or trialkylammonium with 1 to 4 carbon atoms in each alkyl moiety (which may be straight-chain or branched), a sodium ion or a potassium ion, or represents half of a magnesium ion or of a calcium ion.

As examples of the alcohols, mercaptans, phenols, thiophenols, carboxylic acids and thiocarboxylic acids (III) and their salts (IV) that can be used according to the invention, there may be mentioned: methanol, ethanol, propanol, isopropanol, tert.-butanol, allyl alcohol, propargyl alcohol, 3-methylbutynol-(3), butenol-(3), 2-chloroethanol, 4-chloro-2-butynol, cyclohexanol, glycol monomethyl ether, benzyl alcohol, materials according to process variant (a), the reaction is represented by the following equation:

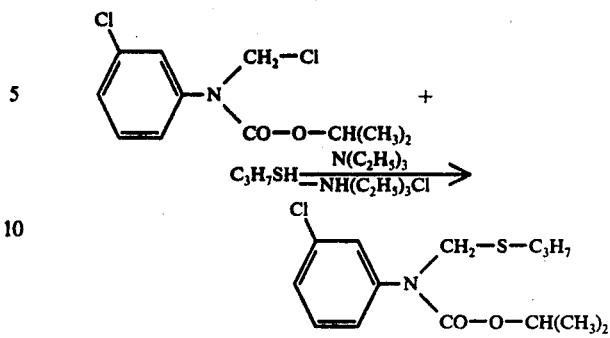

If Isopropyl-N-chloromethyl-N-(3-chlorophenyl)-carbamate and sodium acetate are used as the starting materials according to process variant (b), the course of the reaction can be represented by the following equation:

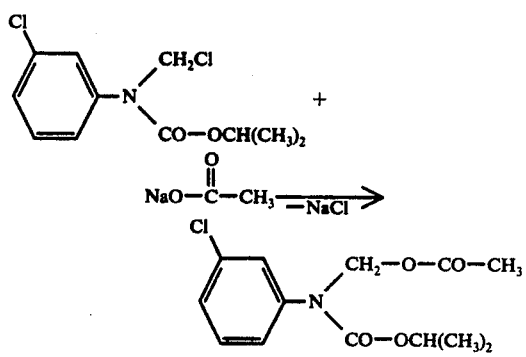

As examples of the N-chloromethyl-N-aryl carbamates (II) that can be used according to the invention, there may be mentioned: Isopropyl-N-chloromethyl-N-phenyl carbamate, 2-Chloroethyl-N-chloromethyl-N-phenylcarbamate, Isopropyl-N-chloromethyl-N-(3-chlorophenyl)-carbamate, 2-Chloroethyl-N-chloromethyl-N-(3-chlorophenyl)-carbamate, 4-Chloro-2-butynyl-N-chloromethyl-N-(3-chlorophenyl)-carbamate, 3-Butynyl-N-chloromethyl-N-(3-chlorophenyl)-carbamate, 2,4-dichlorophenol, 4-chlorophenol, methylmercaptan, ethylmercaptan, propylmercaptan, isopropylmercaptan, allylmercaptan, benzylmercaptan, 4-chlorothiophenol, sodium formate, sodium acetate, sodium monochloroacetate, sodium dichloroacetate, sodium 2,2-dichloropropionate, sodium phenylacetate, sodium benzoate, potassium acetate, sodium thioacetate, sodium butyrate, sodium valerate, sodium propionate, sodium isobutyrate, sodium trifluoroacetate, sodium laevuleate, sodium cretonate, sodium salt of succinic acid monoester, sodium salt of maleic acid monoester and sodium salt of fumaric acid mono ester.

The alchols, mercaptans, phenols, thiophenols, carboxylic acids and thiocarboxylic acids as well as their salts, which correspond to the formulae (III) and (IV) are used as starting substances, are known.

As a diluent in the reaction according to process variant (a) there may be used any inert organic solvent, especially a hydrocarbon, such as benzine, benzene or toluene, a halogenated hydrocarbon, such as dichloromethane, chloroform or carbon tetrachloride, or an ether, such as diethyl ether, dioxane or tetrahydrofuran.

Any customary acid-binder can be used as the acid-binding agent, but it is preferred to use an alkali metal hydroxide, an alkali metal carbonate or a tertiary organic base: sodium carbonate, triethylamine and pyridine are particularly suitable.

The reaction temperatures in process variant (a) can be varied over a fairly wide range. In general, the reaction is carried out at from $-20°$ to $+100°$ C, preferably from $-10°$ to $+80°$ C.

In carrying out process variant (a) 1 to 1.5 moles of the compound of the formula (III) and 1 and 2 moles of an acid-binding agent are preferably used per mole of N-chloromethyl N-arylcarbamic acid ester of the formula (II). A further excess over the stoichiometric amounts does not result in any significant improvement in yield.

In order to isolate the compounds of the formula (I), the hydrochloride or chloride produced is removed by filtering it and then thoroughly rinsing the reaction solution with water; the solution is dried over freshly calcined sodium sulphate and subsequently distilled. The compounds of the formula (I) are mostly water-clear liquids that can easily be distilled. In some cases, however, oils that cannot be distilled are obtained.

As a diluent for the reaction according to process variant (b), there may be used any polar organic solvent, preferably a nitrile, such as acetonitrile and tolunitrile, a sulphoxide, such as dimethylsulphoxide, or an amide, such as dimethylformamide.

The reaction temperatures for process variant (b) can be varied over a fairly wide range. In general, the reaction is carried out at from 0° to 150° C, preferably from 20° to 10° C.

In carrying out process variant (b), 1 mole of the compound of the formula (IV) is generally employed per mole of the compound of the formula (II).

In order to isolate the compound of the formula (I), the chloride produced is filtered off, the filtrate is evaporated to dryness and the residue is taken up in an organic solvent. After brief shaking with water, the organic phase is dried and thereafter the solvent is distilled off in vacuo. The product thus obtained is in many cases pure but can be further purified by distillation, if necessary.

The preparation of compounds of this invention and the process employed is illustrated in and by the following preparative Examples.

EXAMPLE 1

Preparation of Isopropyl-N-methoxymethyl-N-phenyl carbamate

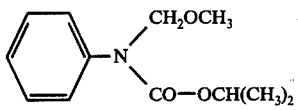

A mixture of 23.9 g (0.746 mole) of methanol and 37.8 g (0.373 mole) of triethylamine in 95 ml of anhydrous benzene was slowly added dropwise, whilst stirring, to a solution of 84.9 g (0.373 mole) of N-Isopropyl-N-chloromethyl-N-phenyl carbamate in 200 ml of anhydrous benzene at 20° C. The exothermic reaction was kept to 20° C by means of an ice bath. Thereafter, the triethylamine hydrochloride was filtered off and the benzene solution was washed with water and dried over freshly calcined sodium sulphate. The Isopropyl-N-methoxymethyl-N-phenylcarbamate thus obtained was purified by distillation; 74.9 g (90% of theory) of boiling point 97° – 98° C/0.45 mm Hg were obtained.

EXAMPLE 2

Preparation of Isopropyl-N-propylmercaptomethyl-N-(3-chlorophenyl)-carbamate

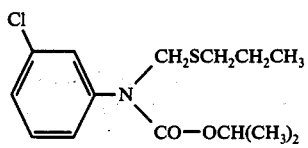

A mixture of 15.2 g (0.2 mole) of n-propylmercaptan and 24.2 g (0.24 mole) of triethylamine in 160 ml of anhydrous benzene was added dropwise, whilst stirring, to a solution of 52.4 g (0.2 mole) of Isopropyl-N-chloromethyl-N-(3-chlorophenyl)-carbamate in 200 ml of anhydrous benzene at 20° C. The temperature was kept at 20° C. Thereafter, the mixture was heated for one hour under reflux. After cooling, the triethylamine hydrochloride produced was filtered off and the resulting benzene solution was washed with water and dried over freshly calcined sodium sulphate. After distilling off the solvent, an oil remained, which was distilled in vacuo. 51.9 g (86% of theory) of Isopropyl-N-propyl-mercaptomethyl-N-(3-chlorophenyl)-carbamate of boiling point 158° C/1 mm Hg were obtained.

EXAMPLE 3

Preparation of Methyl-N-(2,4-dichlorophenoxymethyl)-N-(4-chlorophenyl)-carbamate

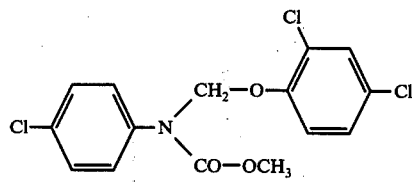

A solution of 16.3 g (0.1 mole) of 2,4-dichlorophenol and 14 ml (0.1 mole) of triethylamine in 100 ml of benzene was added dropwise, over the course of 15 minutes, to a solution of 23.4 g (0.1 mole) of Methyl-N-chloromethyl-N-(4-chlorophenyl)-carbamate in 200 ml of dry benzene. Thereafter the triethylamine hydrochloride was filtered off, the filtrate was washed with 5% strength sodium hydroxide solution and water, and after drying over calcined sodium sulphate the benzene was distilled off under reduced pressure. 52.4 g (92% of theory) of Methyl-N-(2,4-dichlorophenoxymethyl)-N-(4-chlorophenyl)-carbamate, melting at 70° – 80° C after recrystallization from ethanol, were obtained.

EXAMPLE 4

Preparation of Isopropyl-N-acetoxymethyl-N-(3-chlorophenyl)-carbamate

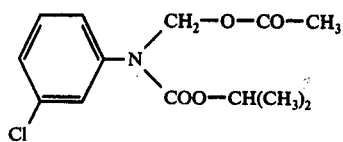

A mixture of 52.4 g (0.2 mole) of Isopropyl-N-chloromethyl-N-(3-chlorophenyl)-carbamate and 24.6 g (0.3 mole) of anhydrous sodium acetate in 700 ml of anhydrous acetonitrile was boiled for four hours under reflux. After cooling, the salts were filtered off, the filtrate was evaporated, the residue was dissolved in 300 ml of ether and the ether solution was washed with water and dried over freshly calcined sodium sulfate. Thereafter, the solvent was distilled off and the resulting oil was distilled in vacuo. 34.2 g (95% of theory) of Isopropyl-N-acetoxymethyl-N-(3-chlorophenyl)-carbamate of boiling point 134° C/0.3 mm Hg and refractive index $n_D^{20}$ 1.5074 were obtained.

The following compounds may be prepared by methods analogous to those given in the foregoing Examples.

Table 1

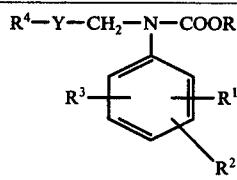

| Compound No. | R | $R^1$ | $R^2$ | $R^3$ | Y | $R^4$ | Compound Name | Melting Point, °C / Boiling point, °C/mm Hg / Refractive index $n_D^{20}$ |
|---|---|---|---|---|---|---|---|---|
| 1 | $CH_3$ | H | H | H | O | $CH_3$ | Methyl-N-methoxymethyl-N-phenyl carbamate | 86–87/0.3 |
| 2 | $CH_3$ | H | H | H | O | $C_2H_5$ | Methyl-N-ethoxymethyl-N-phenyl carbamate | 104/0.35 |
| 3 | $CH_3$ | H | H | H | O | $(CH_3)_2CH$ | Methyl-N-isopropoxymethyl-N-phenyl carbamate | 79–81/0.15 |
| 4 | $CH_3$ | H | H | H | O | $C_4H_9$ | Methyl-N-n-butoxymethyl-N-phenyl carbamate | 93–94/0.15 |
| 5 | $(CH_3)_2CH$ | H | H | H | O | $CH_3$ | Isopropyl-N-methoxymethyl-N-phenyl carbamate | 98/0.4 |
| 6 | $(CH_3)_2CH$ | H | H | H | O | $C_2H_5$ | Isopropyl-N-ethoxyethyl-N-phenyl carbamate | 92/0.3 |
| 7 | $(CH_3)_2CH$ | H | H | H | O | $C_3H_7$ | Isopropyl-N-n-propoxymethyl-N-phenyl carbamate | 128–130/0.8 |
| 8 | $(CH_3)_2CH$ | H | H | H | O | $(CH_3)_2CH$ | Isopropyl-N-isopropoxymethyl-N-phenyl carbamate | 94/0.2 |
| 9 | $(CH_3)_2CH$ | 3-Cl | H | H | O | $CH_3$ | Isopropyl-N-methoxymethyl-N-3-chlorophenyl carbamate | 110/0.2 |

(Compounds 10 to 43 hereinbelow have not been named for the sake of brevity, inasmuch as the nomenclature is analogous to that given above.)

| Compound No. | R | $R^1$ | $R^2$ | $R^3$ | Y | $R^4$ | Melting point, °C / Boiling point, °C/mm Hg / Refractive index $n_D^{20}$ |
|---|---|---|---|---|---|---|---|
| 10 | $(CH_3)_2CH$ | 3-Cl | H | H | O | $C_2H_5$ | 131–133/0.5 |
| 11 | $(CH_3)_2CH$ | 3-Cl | H | H | O | $C_3H_7$ | 139–141/0.5 |
| 12 | $(CH_3)_2CH$ | 3-Cl | H | H | O | $(CH_3)_2CH$ | 133–135/0.5 |
| 13 | $(CH_3)_2CH$ | 3-Cl | H | H | O | $C_4H_9$ | 146–148/0.5 |
| 14 | $(CH_3)_2CH$ | 3-Cl | H | H | O | $CH\equiv C-CH_2$ | 135–140/0.3 |
| 15 | $(CH_3)_2CH$ | 3-Cl | H | H | O | $(C_2H_5)(CH_3)CH$ | 135–137/0.4 |
| 16 | $(CH_3)_2CH$ | 3-Cl | H | H | O | $(CH_3)_3C$ | 130–132/0.3 |
| 17 | $(CH_3)_2CH$ | 3-Cl | H | H | O | $CH_2=CH-C(CH_3)_2$ | 139–141/0.3 |
| 18 | $(CH_3)_2CH$ | 3-Cl | H | H | O | $HC\equiv C-C(CH_3)_2-$ | 140–145/0.4 |
| 19 | $ClCH_2CH_2$ | 3-Cl | H | H | O | $CH_3$ | 1.5380 |
| 20 | $ClCH_2CH_2$ | 3-Cl | H | H | O | $C_2H_5$ | 1.5325 |
| 21 | $ClCH_2CH_2$ | 3-Cl | H | H | O | $C_3H_7$ | 1.5276 |
| 22 | $ClCH_2CH_2$ | 3-Cl | H | H | O | $(CH_3)_2CH$ | 1.5282 |
| 23 | $ClCH_2CH_2$ | 3-Cl | H | H | O | $C_4H_9$ | 1.5239 |
| 24 | $ClCH_2CH_2$ | 3-Cl | H | H | O | $(C_2H_5)(CH_3)CH$ | 1.5274 |
| 25 | $ClCH_2CH_2$ | 3-Cl | H | H | S | $C_3H_7$ | 1.5548 |
| 26 | $ClCH_2CH_2$ | 3-Cl | H | H | S | $C_4H_9$ | 1.5496 |
| 27 | $CH_3$ | 3-Cl | H | H | O | $CH_3$ | 96–98/0.25 |
| 28 | $CH_3$ | 3-Cl | H | H | O | $(CH_3)_2CH$ | 96–97/0.15 |
| 29 | $CH_3$ | 3-Cl | H | H | O | $C_4H_9$ | 125–126/0.5 |
| 30 | $CH_3$ | H | 4-Cl | H | O | $CH_3$ | 113/0.4 |
| 31 | $CH_3$ | H | 4-Cl | H | O | $(CH_3)_2CH$ | 111/0.25 |
| 32 | $CH_3$ | H | 4-Cl | H | O | $C_4H_9$ | 118–119/0.25 |
| 33 | $CH_3$ | 3-Cl | 4-Cl | H | O | $CH_3$ | 154–155/1.5 |
| 34 | $CH_3$ | 3-Cl | 4-Cl | H | O | $C_2H_5$ | 136/0.35 |
| 35 | $CH_3$ | 3-Cl | 4-Cl | H | O | $(CH_3)_2CH$ | 122–123/0.25 |
| 36 | $CH_3$ | 3-Cl | 4-Cl | H | O | $C_4H_9$ | 166–167/1.3 |
| 37 | $CH_3$ | H | H | H | O | $2,4-Cl_2-C_6H_3$ | 72–72.5 |
| 38 | $CH_3$ | H | H | H | S | $C_4H_9$ | 124–126/0.65 |
| 39 | $CH_3$ | H | H | H | S | $4-Cl-C_6H_4$ | 171–175/0.15 |
| 40 | $(CH_3)_2CH$ | 2-$CH_3$ | H | 5-Cl | O | $CH_3$ | 132/0.6 |
| 41 | $(CH_3)_2CH$ | 2-$CH_3$ | H | 5-Cl | O | $C_2H_5$ | 130/0.2 |
| 42 | $(CH_3)_2CH$ | 2-$CH_3O$ | H | 5-Cl | O | $CH_3$ | 138/0.2 |

Table 1-continued $$R^4-Y-CH_2-N-COOR$$ on phenyl ring with $R^3$, $R^1$, $R^2$ substituents

| No. | R | R¹ | R² | | | R⁴ | |
|---|---|---|---|---|---|---|---|
| 43 | $(CH_3)_2CH$ | 2-$CH_3O$ | H | 5-Cl | O | $C_2H_5$ | 138/0.3 |

Table 2

(V)

Structure:
$$R^1, R^2, R^3 \text{ substituted phenyl-N}(CO-O-R)(CH_2-Y-\overset{Y}{\underset{\|}{C}}-R^4)$$

| Compound No. | R | R¹ | R² | R³ | Y | R⁴ | Compound Name | Melting point, °C Boiling point, °C/mm Hg Refractive index $n_D^{20}$ |
|---|---|---|---|---|---|---|---|---|
| 44 | $(CH_3)_2CH$ | H | H | H | O | $(CH_3)_2CH$ | Isopropyl-N-2-methyl propanoyl-oxymethyl-N-phenyl carbamate | 122/0.3 |
| 45 | $(CH_3)_2CH$ | H | H | H | O | $(CH_3)_3C$ | Isopropyl-2,2-dimethyl propanoyl-N-oxymethyl-N-phenyl carbamate | 138/0.7 |
| 46 | $(CH_3)_2CH$ | H | H | H | O | $C_6H_5-CH_2$ | Isopropyl-N-2-phenyl-acetoxymethyl-N-phenyl carbamate | 179–180/0.5 |
| 47 | $(CH_3)_2CH$ | H | H | H | O | $C_6H_5$ | Isopropyl-N-benzoyloxy-methyl-N-phenyl carbamate | 64–65 |
| 48 | $(CH_3)_2CH$ | H | H | H | O | H | Isopropyl-N-2-formyloxy-methyl-N-phenyl carbamate | 117/0.35 |
| 49 | $(CH_3)_2CH$ | H | H | H | O | $CH_3$ | Isopropyl-N-acetoxymethyl-N-phenyl carbamate | 118/0.4 |
| 50 | $(CH_3)_2CHl$ | H | H | H | O | $C_2H_5$ | Isopropyl-N-N-propanoyl-oxymethyl-N-phenyl carbamate | 119/0.2 |
| 51 | $(CH_3)_2CH$ | 3-Cl | H | H | O | $C_2H_5$ | Isopropyl-N-n-propanoyl-oxymethyl-N-3-chlorophenyl carbamate | 138/0.4 |
| 52 | $(CH_3)_2CH$ | 3-Cl | H | H | O | $C_3H_7$ | Isopropyl-N-n-butanoyloxy-methyl-N-3-chlorophenyl carbamate | 150/0.4 |
| 53 | $(CH_3)_2CH$ | 3-Cl | H | H | O | $C_4H_9$ | Isopropyl-N-n-pentanoyloxy-methyl-N-3-chlorophenyl carbamate | 155/0.4 |
| 54 | $(CH_3)_2CH$ | 3-Cl | H | H | O | $(C_2H_5)(CH_3)CH$ | Isopropyl-N-2-methylbutanoyl-oxymethyl-N-3-chlorophenyl carbamate | 147/0.4 |

| Compound No. | R | R¹ | R² | R³ | Y | R⁴ | Melting Point, °C Boiling point, °C/mm Hg Refractive index $n_D^{20}$ |
|---|---|---|---|---|---|---|---|
| 55 | $(CH_3)_2CH$ | 3-Cl | H | H | O | $(CH_3)_2CH$ | 142/0.5 |
| 56 | $(CH_3)_2CH$ | 3-Cl | H | H | O | $(CH_3)_3C$ | 142/0.5 |
| 57 | $(CH_3)_2CH$ | 3-Cl | H | H | O | $ClCH_2$ | 1.5184 |
| 58 | $(CH_3)_2CH$ | 3-Cl | H | H | O | $Cl_2CH$ | 1.5203 |
| 59 | $(CH_3)_2CH$ | 3-Cl | H | H | O | $CCl_3$ | 1.5249 |
| 60 | $(CH_3)_2CH$ | 3-Cl | H | H | O | $CH_3CCl_2$ | 1.5146 |
| 61 | $(CH_3)_2CH$ | 3-Cl | H | H | O | $C_6H_5$ | 51 |
| 62 | $(CH_3)_2CH$ | 3-Cl | H | H | O | $C_6H_5CH_2$ | 1.5374 |
| 63 | $(CH_3)_2CH$ | 2-$CH_3O$ | H | 5-Cl | O | $CH_3$ | 1.5086 |
| 64 | $(CH_3)_2CH$ | 2-$CH_3$ | H | 5-Cl | O | $CH_3$ | 1.5049 |
| 65 | $ClCH_2CH_2$ | 3-Cl | H | H | O | $CH_3$ | 160/0.1 |
| 66 | $ClCH_2CH_2$ | 3-Cl | H | H | O | $ClCH_2$ | 188/0.1 |
| 67 | $CH_3$ | H | H | H | S | $C_2H_5$ | 1.5848 |
| 68 | $ClCH_2CH_2$ | 3-Cl | H | H | O | 2,4-$Cl_2-C_6H_3$ | 82 |
| 69 | $ClCH_2CH_2$ | 3-Cl | H | H | O | $C_2H_5$ | 190/1.2 |
| 70 | $ClCH_2CH_2$ | 3-Cl | H | H | O | $(CH_3)_2CH$ | 170/0.6 |

Table 3

$$R^4-Y-CH_2-N-COOR \quad (I)$$

(with phenyl ring bearing $R^1$, $R^2$, $R^3$)

| Compound No. | R | $R^1$ | $R^2$ | $R^3$ | Y | $R^4$ | Compound Name | Boiling point, °C/mm Hg |
|---|---|---|---|---|---|---|---|---|
| 71 | HC≡C—CH(CH₃) | 3-Cl | H | H | O | CH₃ | 3-Butin-2-yl-N-methoxymethyl-N-3-chlorophenyl-carbamate | 136–137/0.3 |
| 72 | HC≡C—CH(CH₃) | 3-Cl | H | H | O | C₂H₅ | 3-Butin-2-yl-N-ethoxymethyl-N-3-chlorophenyl carbamate | 140–141/0.4 |
| 73 | HC≡C—CH(CH₃) | 3-Cl | H | H | O | n-C₃H₇ | 3-Butin-2-yl-N-n-propoxymethyl-N-3-chlorophenyl carbamate | 140–142/0.2 |
| 74 | HC≡C—CH(CH₃) | 3-Cl | H | H | O | (CH₃)₂CH | 3-Butin-2-yl-N-isopropoxymethyl-N-3-chlorophenyl carbamate | 142–143/0.5 |
| 75 | HC≡C—CH(CH₃) | 3-Cl | H | H | O | (CH₃)₂CH—CH₂ | 3-Butin-2-yl-N-3-methyl-i-butoxymethyl-N-3-chlorophenyl carbamate | 148–149/0.4 |
| 76 | HC≡C—C(CH₃)₂ | 3-Cl | H | H | O | CH₃ | 3-Butin-2-yl-N-methoxymethyl-N-3-chlorophenyl carbamate | 132–134/0.1 |
| 77 | HC≡C—C(CH₃)₂ | 3-Cl | H | H | O | (CH₃)₂CH | 3-Butin-2-yl-N-isopropoxymethyl-N-3-chlorophenyl carbamate | 140–141/0.6 |

Table 4

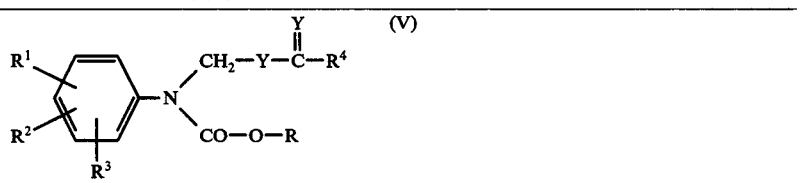

(V)

| Compound No. | R | $R^1$ | $R^2$ | $R^3$ | Y | $R^4$ | Compound Name | Melting point, °C / Boiling point, °C/mm Hg / Refractive index $N_D^{20}$ |
|---|---|---|---|---|---|---|---|---|
| 78 | (CH₃)₂CH | 2-CH₃O | 5-Cl | H | O | CH₂Cl | Isopropyl-N-chloroacetoxymethyl-N-(2-methoxy-5-chlorophenyl) carbamate | 72.5 |
| 79 | (CH₃)₂CH | 2-CH₃O | 5-Cl | H | O | CCl₂CH₃ | Isopropyl-N-(3,3-dichloro-n-propanoyloxymethyl)-N-(2-methy-5-chlorophenyl) carbamate | 1.5167 |
| 80 | (CH₃)₂CHCH₂ | 3-Cl | H | H | O | CH₃ | Isobutyl-N-acetoxymethyl-N-3-chlorophenyl carbamate | 153/0.1 |
| 81 | (CH₃)₂CHCH₂ | 3-Cl | H | H | O | C₂H₅ | Isobutyl-N-n-propanoyloxymethyl-N-3-chlorophenyl carbamate | 151/0.1 |
| 82 | (CH₃)₂CHCH₂ | 3-Cl | H | H | O | n-C₃H₇ | Isobutyl-N-n-butanoyloxymethyl-N-3-chlorophenyl carbamate | 159/0.1 |
| 83 | (CH₃)₂CHCH₂ | 3-Cl | H | H | O | cyclo-C₃H₅ | Isobutyl-N-cyclopropylcarbonyloxymethyl-N-3-chlorophenyl carbamate | 168/0.1 |
| 84 | (CH₃)₂CHCH₂ | 3-Cl | H | H | O | C(CH₃)₃ | Isobutyl-N-(2,2-dimethylpropanoyloxymethyl)-N-3-chlorophenyl carbamate | 161/0.1 |
| 85 | C₂H₅—CH(CH₃) | 3-Cl | H | H | O | CH₃ | 1-Methylpropyl-1-N-acetoxymethyl-N-3-chlorophenyl carbamate | 145/0.08 |
| 86 | C₂H₅—CH(CH₃) | 3-Cl | H | H | O | C₂H₅ | 1-Methylpropyl-1-N-n-propanoyloxymethyl-N-3-chlorophenyl carbamic acid n-butyl-(2) ester | 150/0.1 |

Table 4-continued $$\text{(V)}$$

Structure: Phenyl ring with substituents R¹, R², R³; N attached bearing CH₂—Y—C(=Y)—R⁴ and CO—O—R groups.

| Compound No. | R | R¹ | R² | R³ | Y | R⁴ | Compound Name | Melting point, °C / Boiling point, °C/mm Hg / Refractive index $N_D^{20}$ |
|---|---|---|---|---|---|---|---|---|
| 87 | C₂H₅—CH(CH₃)— | 3-Cl | H | H | O | n-C₃H₇ | | 156/0.05 |
| 88 | C₂H₅—CH(CH₃)— | 3-Cl | H | H | O | n-C₄H₉ | | 160/0.1 |
| 89 | C₂H₅—CH(CH₃)— | 3-Cl | H | H | O | C(CH₃)₃ | | 153/0.1 |
| 90 | ClCH₂CH₂ | 3-Cl | H | H | O | 2,4-dichlorophenoxymethyl | | 80–82 |
| 91 | ClCH₂CH₂ | 3-Cl | H | H | O | C₃H₇ | | 168/0.6 |
| 92 | ClCH₂CH₂ | 3-Cl | H | H | O | 4-chlorophenyl | | 92–93 |
| 93 | (CH₃)₂CH | H | H | H | O | (C₂H₅)₂CH | | 134/0.3 |
| 94 | (CH₃)₂CH | H | H | H | O | C₃H₇ | | 128/0.3 |
| 95 | (CH₃)₂CH | H | H | H | O | CH₃—CH(Cl)— | | 138/0.4 |
| 96 | (CH₃)₂CH | H | H | H | O | ClCH₂ | | 139/0.3 |
| 97 | (CH₃)₂CH | H | H | H | O | C₂H₅—CH(CH₃)— | | 1.4888 |
| 98 | (CH₃)₂CH | H | H | H | O | C₄H₉ | | 1.4892 |
| 99 | (CH₃)₂CH | H | H | H | O | (CH₃)₂CH—CH₂ | | 1.4868 |
| 100 | (CH₃)₂CH | H | H | H | O | cyclohexyl | | 1.5060 |
| 101 | (CH₃)₂CH | H | H | H | O | cyclohexenyl | | 64.65 |
| 102 | (CH₃)₂CH | H | H | H | O | (CH₃)₃C—CH(Cl)— | | 1.5004 |
| 103 | HC≡C—CH(CH₃)— | 3-Cl | H | H | O | CH₃ | | 153–155°/0.2 |
| 104 | HC≡C—CH(CH₃)— | 3-Cl | H | H | O | ClCH₂ | | 137–139/10⁻³ |
| 105 | HC≡C—CH(CH₃)— | 3-Cl | H | H | O | C₂H₅ | | 155–156/0.2 |
| 106 | HC≡C—CH(CH₃)— | 3-Cl | H | H | O | C₃H₇ | | 158–160/0.1 |
| 107 | HC≡C—CH(CH₃)— | 3-Cl | H | H | O | (CH₃)₂CH | | 154–155/0.2 |

Table 4-continued $$\underset{R^3}{\underset{R^2}{R^1}}\text{—N}\overset{CH_2-Y-\overset{\overset{Y}{\|}}{C}-R^4}{\underset{CO-O-R}{}} \quad (V)$$

| Compound No. | R | R¹ | R² | R³ | Y | R⁴ | Compound Name | Melting point, °C Boiling point, °C/mm Hg Refractive index $N_D^{20}$ |
|---|---|---|---|---|---|---|---|---|
| 108 | CH₃ / HC≡C—CH | 3-Cl | H | H | O | C₄H₉ | | 163–165/0.2 |
| 109 | HC≡C—C(CH₃)₂ | 3-Cl | H | H | O | CH₃ | | 160–162/0.2 |
| 110 | HC≡C—C(CH₃)₂ | 3-Cl | H | H | O | C₂H₅ | | 162–163/0.1 |
| 111 | (CH₃)₂CH | H | H | H | O | CH₃—CO—CH₂—CH₂ | | 71–72 |
| 112 | (CH₃)₂CH | H | H | H | O | CH₃—(CH₂)₁₂— | | 37–38 |
| 113 | (CH₃)₂CH | H | H | H | O | CH₃—(CH₂)₁₄— | | 43–44 |
| 114 | (CH₃)₂CH | H | H | H | O | CH₃—CH=CH— | | 52–53 |
| 115 | (CH₃)₂CH | H | H | H | O | C₄H₉—CH / C₂H₅ | | 1.4845 |
| 116 | (CH₃)₂CH | H | H | H | O | CH₃—(CH₂)₁₀— | 1.4829 | |
| 117 | (CH₃)₂CH | H | H | H | O | ClCH₂CH₂ | | 142–144/0.4 |
| 118 | (CH₃)₂CH | H | H | H | O | Cl₂CH | | 162–163/0.7 |
| 119 | (CH₃)₂CH | H | H | H | O | CH₃O—CO—CH₂—CH₂ | | 39–41 |
| 120 | (CH₃)₂CH | H | H | H | O | CH₂=C— / CH₃ | | 136/0.4 |
| 121 | (CH₃)₂CH | H | H | H | O | CH₂=CH—(CH₂)₈— | | 1.4899 |
| 122 | (CH₃)₂CH | H | H | H | O | CH₂=CH— | | 161/2.5 |
| 123 | (CH₃)₂CH | H | H | H | O | (CH₃)₃C—⟨phenyl⟩— | | 1.5331 |
| 124 | (CH₃)₂CH | H | H | H | O | CH₂—(CH₂)₁₆ | | 35–37 |
| 125 | (CH₃)₂CH | H | H | H | O | Cl—⟨phenyl⟩—CH—CH / CH₃  Cl | | 1.5414 |
| 126 | (CH₃)₂CH | H | H | H | O | 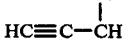 | | 99–100 |

The active compounds according to the invention interfere with the physiological phenomena of plant growth and can therefore be used as plant growth regulators.

The different effects of the active compounds essentially depend on the point in time at which they are used, relative to the stage of development of the seed or of the plant, and on the concentrations employed.

Plant-growth regulators are used for various purposes that are related to the state of development of the plant.

Thus, the seed dormancy can be broken by means of plant-growth regulators in order to cause the seeds to germinate at a certain time that is desired, but at which the seed itself displays no readiness to germinate. Seed germination itself can be either inhibited or promoted by such active compounds depending on the concentration employed. This inhibition or promotion refers to the development of the seedling.

The bud dormancy of plants, that is to say the endogenic annual cycle, can be influenced by the active compounds, so that the plants, for example, shoot or blossom at a point in time at which they normally show no readiness to shoot or blossom.

It is also possible to delay the opening of buds, for example in order to prevent frost damage in areas subject to frost.

The shoot growth or root growth can be promoted or inhibited by the active compounds, depending on the concentration. Thus, it is possible, for example, very greatly to inhibit the growth of the fully formed plant or conversely to bring the plant altogether to a more robust habitus, or to bring about stunted growth.

The inhibition of growth at the edges of roads and paths is of economic interest. Furthermore, the frequency of cutting the grass (mowing) of lawns can be reduced. Equally, the growth of woodlands can be inhibited.

During the growth of the plant, the lateral branching can also be increased by chemically breaking the apical dominance. Interest in this exists, for example, in the propagation of plants by cuttings. Depending on the concentration, it is however also possible to inhibit the growth of side shoots, for example in order to prevent the formation of side shoots in tobacco plants after decaptitation and thereby promote leaf growth.

Growth regulators can also be used to reduce the transpiration rate of plants in order to prevent damage through drying out.

In the case of influencing blossom formation, either a retardation of blossom formation or an acceleration of blossom formation can be achieved depending on the concentration and on the point in time at which the substance is used. Under certain circumstances it is also possible to increase the setting of blossoms, and these effects arise if the appropriate treatments are carried out at the time of normal blossom formation. Furthermore, the formation of predominantly female or predominantly male blossoms can be achieved.

Fruit setting can be promoted, so that more fruit or seedless fruit is formed (parthenocarpy). Under certain conditions, the premature fall of fruit can also be prevented, or the fall of fruit can, to a certain degree, be promoted in the sense of a chemical thining-out. The promotion of the fall of fruit can, however, also be utilized by carrying out the treatment at harvest time, whereby harvesting is facilitated.

Increases in yield by means of growth regulators can be achieved both by promoting the setting of fruit and by the formation of larger fruit or by promotion of vegetative growth. Furthermore, it is possible to stimulate the synthesis or secretion of secondary vegetable constituents (for example the latex secretion of rubber trees).

Some of the active compounds according to the invention show herbicidal properties at higher concentrations. Furthermore, the active compounds according to the invention possess insecticidal, acaricidal and, in some cases, fungitoxic activity.

The active compounds according to the present invention can be converted into the usual formulations, such as solutions, emulsions, suspensions, powders, pestes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents. In the case of the use of water as an extender, organic solvents can, for example, also be used as auxiliary solvents (see Agricultural Chemicals, March 1960, pages 35 to 38).

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated by hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying agents include non-ionic and anionic emulsifiers, such as polyoxyethylene-fatty acid esters, polyoxyethylene-fatty alcohol eithers, for example alkylarylpolyglycol ethers, alkyl sulphonates, alkyl sulphates and aryl sulphonates; and preferred examples of dispersing agents include lignin, sulphite waste liquors and methyl cellulose.

The active compounds according to the invention can be present in the formulations as a mixture with other active substances.

The formulations, in general, contain from 0.1 to 95, preferably from 0.5 to 90, per cent by weight of active compound.

The active compounds can be used as such, in the form of their formulations or in the form of the application forms prepared therefrom, such as ready-to-use solutions, emulsions, suspensions, powders, pastes and granules. They may be employed in any customary manner, for example by watering, spraying, atomising, sprinkling or dusting, The amount of active substance employed can vary over a fairly wide range; it depends essentially on the nature of the desired effect. In general, however, the amounts used are from 0.1 to 25 kg/hectare, preferably from 0.5 to 20 kg/hectare.

The present invention also provides a plant-growth-regulating composition containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants or a plant habitat a compound of the present invention alone or in the form of a composition containing as active ingredient a compound of the present invention in admixture with a diluent or carrier.

The plant-growth-regulating activity of the compounds of the present invention is illustrated in and by the following test Examples.

EXAMPLE A

Growth Inhibition in Grass

Solvent: 10 parts by weight of methanol
Emulsifier: 2 parts by weight of polyethylene-sorbitan monolaurate.

In order to prepare a suitable preparation of the active compound, 1 part by weight of the active compound was mixed with the indicated amounts of solvent and emulsifier and made up to the desired concentration with water.

Grass plants 3 to 4 cm high were sprayed with the active-compound preparations until dripping wet. After 14 days, the additional growth was measured and the inhibition of growth in per cent of the additional growth of the control plants was calculated. The damage was classified on a scale from 0 to 5, with "0" denoting no damage and "5" denoting the death of the plants.

The active compounds, active-compound concentrations and results can be seen from Table A below:

Table A

Inhibition of growth in grass (*Festuca pratensis*)

| Active compound | Concentration (ppm) | Inhibition/damage |
|---|---|---|
| 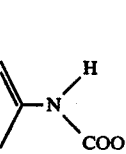 (known) | 2000<br>1000<br>500 | 70 % / 3<br>55 % / 2<br>55 % / 1 |
| 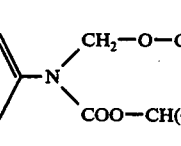 (known) | 2000<br>1000<br>500 | — / 5<br>— / 5<br>30 % / 4 |
| 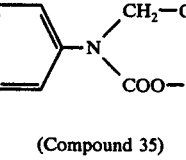 (Compound 9) | 2000<br>1000<br>500 | 100 % / 1<br>100 % / 1<br>40 % / 1 |
| 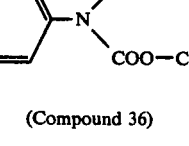 (Compound 35) | 1000 | 60 % / 1 |
| 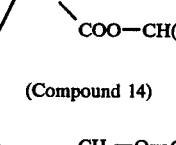 (Compound 36) | 1000 | 60 % / 0 |
| 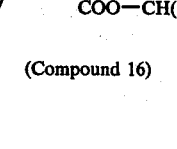 (Compound 14) | 1000 | 100 % / 2 |
|  (Compound 16) | 1000 | 60 % / 0 |

Table A-continued

Inhibition of growth in grass (*Festuca pratensis*)

| Active compound | Concentration (ppm) | Inhibition/damage |
|---|---|---|
| (Compound 18) 3-Cl-C$_6$H$_4$-N(CH(CH$_3$)-O-C(CH$_3$)$_2$-C≡CH)(COO-CH(CH$_3$)$_2$) | 1000 | 80 % / 1 |
| (Example 4, supra) 3-Cl-C$_6$H$_4$-N(CH$_2$-O-CO-CH$_3$)(COO-CH(CH$_3$)$_2$) | 500 | 90 % / 0 |
| (Compound 57) 3-Cl-C$_6$H$_4$-N(CH$_2$-O-CO-CH$_2$Cl)(COO-CH(CH$_3$)$_2$) | 500 | 90 % / 1 |
| (Compound 58) 3-Cl-C$_6$H$_4$-N(CH$_2$-O-CO-CHCl$_2$)(COO-CH(CH$_3$)$_2$) | 500 | 90 % / 0 |

EXAMPLE B

Inhibition of Growth in Cress Seedlings

Solvent: 10 parts by weight of methanol
Emulsifier: 2 parts by weight of polyethylene-sorbitan monolaurate.

In order to prepare a suitable preparation of the active compound, 1 part by weight of active compound was mixed with the indicated amounts of solvent and emulsifier and made up to the desired concentration with water.

50 cress seeds were placed on a filter paper onto which the active-compound preparation had been dripped. Since the cress seeds adhere to moist filter paper, the latter was placed vertically in a beaker of 250 ml capacity. The beaker was filled with 20 ml of active-compound preparation and was covered with a glass plate. After 4 days the seedlings were measured and the percentage inhibition of elongation growth was calculated, relative to the control (distilled water with the appropriate amounts of solvent and emulsifier).

The active compounds, active-compound concentrations and results are shown in Table B below:

Table B

Inhibition of growth in cress seedlings

| Active Compound | Concentration (ppm) | Inhibition |
|---|---|---|
| Maleic hydrazide (known) | 200 | 35 % |
| 3-Cl-C$_6$H$_4$-NH-COO-CH(CH$_3$)$_2$ (known) | 200 | 40 % |
| (Compound 9) 3-Cl-C$_6$H$_4$-N(CH$_2$-O-CH$_3$)(COO-CH(CH$_3$)$_2$) | 200 | 55 % |
| (Compound 14) 3-Cl-C$_6$H$_4$-N(CH$_2$-O-CH$_2$-C≡CH)(COO-CH(CH$_3$)$_2$) | 200 | 70 % |

Table B-continued
Inhibition of growth in cress seedlings

| Active Compound | Concentration (ppm) | Inhibition |
|---|---|---|
| (Compound 16) 3-Cl-C6H4-N(CH2-O-C(CH3)3)(COO-CH(CH3)2) | 200 | 50% |
| (Compound 18) 3-Cl-C6H4-N(CH-O-C(CH3)2-C≡CH)(COO-CH(CH3)2) | 200 | 70% |
| (Example 4) 3-Cl-C6H4-N(CH2-O-CO-CH3)(COO-CH(CH3)2) | 200 | 80% |
| (Compound 57) 3-Cl-C6H4-N(CH2-O-CO-CH2Cl)(COO-CH(CH3)2) | 200 | 80% |
| (Compound 58) 3-Cl-C6H4-N(CH2-O-CO-CHCl2)(COO-CH(CH3)2) | 200 | 80% |

It will be understood that the specification and examples are illustrative but not limitative of the present invention and that other embodiments within the spirit and scope of the invention will suggest themselves to those skilled in the art.

What is claimed is:

1. N-arylcarbamate of the formula

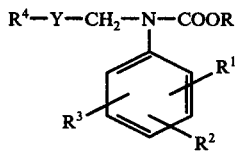

wherein

R is open-chain lower aliphatic hydrocarbyl containing up to ten carbon atoms or open chain substituted lower aliphatic hydrocarbyl wherein the substituents are hydroxy, halogen, alkoxy having 1 to 4 carbon atoms, aryl or substituted aryl having 6 to 10 carbon atoms; said substituted aryl being substituted by at least one member selected from the group consisting of halogen, alkyl of from 1 to 4 carbon atoms, haloalkyl of from 1 to 4 carbon atoms and 1 to 3 halogen atoms, alkoxy of from 1 to 4 carbon atoms and nitro $R^1$, $R^2$, and $R^3$ are individually selected from the group consisting of hydrogen, alkyl and haloalkyl of from 1 to 10 carbon atoms, alkoxy of from 1 to 10 carbon atoms, cycloalkyl of up to 8 carbon atoms and halogen.

$R^4$ is alkyl with 1 to 6 carbon atoms, alkenyl with 3 to 6 carbon atoms, alkynyl with 3 to 6 carbon atoms, haloalkyl with 1 to 6 carbon atoms and 1 to 3 halogen atoms, alkoxyalkyl, alkylthioalkyl, carbalkoxyalkyl and carbalkoxyalkenyl each with 1 to 4 carbon atoms in the alkoxy or alkylthio part and 1 to 4 carbon atoms in the alkyl part, cycloalkyl with 3 to 8 carbon atoms or aryl, aralkyl, aryloxyalkyl or arylthioalkyl with, in each case, 6 to 10 carbon atoms in the aryl part and 1 to 3 carbon atoms in the alkyl part, the aryl part of the four last-mentioned radicals being unsubstituted or substituted by halogen, alkyl with 1 to 3 carbon atoms, alkoxy with 1 to 3 carbon atoms, haloalkyl with 1 to 2 carbon atoms and 1 to 5 halogen atoms and Y is oxygen or sulfur.

2. Compound as claimed in claim 1 wherein R is alkyl of 4 carbon atoms.

3. Compound as claimed in claim 1 wherein R is alkenyl or alkynyl of from 3 to 6 carbon atoms.

4. Compound as claimed in claim 1 wherein R is hydroxyalkyl, hydroxyalkenyl or hydroxyalkynyl of up to 6 carbon atoms.

5. Compound as claimed in claim 1 wherein R is alkoxyalkyl of up to 4 carbon atoms in each alkyl moiety.

6. Compound as claimed in claim 1 wherein R is haloalkyl, haloalkenyl and haloalkynyl of up to 6 carbon atoms and from 1 to 3 halogen atoms.

7. Compound as claimed in claim 1 wherein R is aralkyl of from 1 to 4 carbon atoms in the alkyl moiety and 6 to 10 carbon atoms in the aryl moiety, wherein the aryl moiety may be substituted with at least one member selected from the group consisting of halogen, alkyl of from 1 to 4 carbon atoms, haloalkyl of from 1 to 4 carbon atoms and 1 to 3 halogen atoms, alkoxy of from 1 to 4 carbon atoms and nitro.

8. Compound as claimed in claim 1 wherein $R^1$, $R^2$ and $R^3$ are individually selected from the group consisting of hydrogen, fluorine, chlorine, bromine, alkyl with 1 to 4 carbon atoms, cycloalkyl with 5 to 7 carbon atoms, straight-chain or branched alkoxy with 1 to 4 carbon atoms or haloalkyl with 1 to 2 carbon atoms and 2 to 5 halogen atoms; and $R^4$ is straight-chain or branched alkyl with 1 to 6 carbon atoms or haloalkyl with 1 to 6 carbon atoms and 1 to 3 halogen atoms, straight-chain or branched alkenyl with 3 to 6 carbon atoms, straight-chain or branched alkynyl with 3 to 6 carbon atoms, alkoxyalkyl, alkylthioalkyl or, carbalkoxyalkyl, carbalkoxyalkenyl with 1 to 4 carbon atoms in the alkoxy or alkylthio part and 1 to 4 carbon atoms in the alkyl part, cycloalkyl with 3 to 8 carbon atoms, aryl with 6 to 10 carbon atoms, or an aralkyl, aryloxyalkyl or arylthioalkyl radical with, in each case, 6 to 10 carbon atoms in the aryl moiety and 1 to 3 carbon atoms in the alkyl moiety, the four last-mentioned radicals being substituted or unsubstituted by one or more substituents selected from halogen, straight-chain or branched alkyl or alkoxy with, in either case, 1 to 3 carbon atoms and haloalkyl with 1 to 2 carbon atoms and 1 to 5 halogen atoms.

9. Compound as claimed in claim 1 designated Methyl-N-methoxymethyl-N-phenyl carbamate.

10. Compound as claimed in claim 1 designated Methyl-N-ethoxymethyl-N-phenyl carbamate.

11. Compound as claimed in claim 1 designated Methyl-N-isopropoxymethyl-N-phenyl carbamate.

12. Compound as claimed in claim 1 designated Methyl-N-n-butoxymethyl-N-phenyl carbamate.

13. Compound as claimed in claim 1 designated Isopropyl-N-methoxymethyl-N-phenyl carbamate.

14. Compound as claimed in claim 1 designated Isopropyl-N-ethoxymethyl-N-phenyl carbamate.

15. Compound as claimed in claim 1 designated Isopropyl-N-n-propoxymethyl-N-phenylcarbamate.

16. Plant-growth regulant composition comprising an agriculturally acceptable carrier and, as an active ingredient, plant growth regulatingly effective amounts of a compound as claimed in claim 1.

17. Method of regulating the growth of plants which comprises applying to the plants or their habitat an effective amount of an N-aryl carbamate of the formula

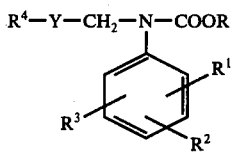

wherein

R is open-chain lower aliphatic hydrocarbyl containing up to 10 carbon atoms or substituted open-chain lower aliphatic hydrocarbyl wherein the substituents are hydroxy, halogen, alkoxy having 1 to 4 carbon atoms or aryl having 6 to 10 carbon atoms.

$R^1$, $R^2$ and $R^3$ are individually selected from the group consisting of hydrogen, alkyl and haloalkyl of from 1 to 10 carbon atoms, alkoxy of from 1 to 10 carbon atoms, cycloalkyl of up to 8 carbon atoms and halogen;

$R^4$ is alkyl with 1 to 6 carbon atoms, alkenyl with 3 to 6 carbon atoms, alkynyl with 3 to 6 carbon atoms, haloalkyl with 1 to 6 carbon atoms and 1 to 3 halogen atoms, alkoxyalkyl alkylthioalkyl, carbalkoxyalkyl and carbalkoxyalkenyl each with 1 to 4 carbon atoms in the alkoxy or alkylthio part and 1 to 4 carbon atoms in the alkyl part, cycloalkyl with 3 to 8 carbon atoms or aryl, aralkyl, aryloxyalkyl or arylthioalkyl with, in each case, 6 to 10 carbon atoms in the aryl part and 1 to 3 carbon atoms in the alkyl part, the aryl part of the four last-mentioned radicals being unsubstituted or substituted by halogen, alkyl with 1 to 3 carbon atoms, alkoxy with 1 to 3 carbon atoms, haloalkyl with 1 to 2 carbon atoms and 1 to 5 halogen atoms and Y is oxygen or sulfur.

18. Method as claimed in claim 17 wherein said compound is selected from the group consisting of Methyl-N-methoxymethyl-N-phenyl carbamate, Methyl-N-ethoxymethyl-N-phenylcarbamate, Methyl-N-isopropoxymethyl-N-phenyl carbamate, Methyl-N-n-butoxymethyl-N-phenyl carbamate, Isopropyl-N-methoxymethyl-N-phenyl carbamate, Isopropyl-N-ethoxymethyl-N-phenyl-carbamate, Isopropyl-N-n-propoxymethyl-N-phenyl carbamate.

19. Method as claimed in claim 17 wherein the growth of plants is stimulated.

20. Method as claimed in claim 17 wherein the growth of plants is retarded.

* * * * *

UNITED STATES PATENT AND TRADEMARK OFFICE
CERTIFICATE OF CORRECTION

PATENT NO. : 4,093,447
DATED : June 6, 1978
INVENTOR(S) : Carl Metzger et al

It is certified that error appears in the above-identified patent and that said Letters Patent are hereby corrected as shown below:

Patent Column 1, line 6, Serial Number of Parent is --265,909-- not "090".

Column 5, line 33, "10°" should be --100°--.

Column 6, line 67, "70°" should be --79°--.

Column 16, "1.4829" belongs in last column (compound 116)

Column 17, line 29, "decaptitation" should be --decapitation--.

Column 17, line 66, "pestes" should be --pastes--.

Signed and Sealed this

Eighth Day of May 1979

[SEAL]

Attest:

RUTH C. MASON
Attesting Officer

DONALD W. BANNER
Commissioner of Patents and Trademarks